(12) United States Patent
Leen et al.

(10) Patent No.: US 11,307,137 B2
(45) Date of Patent: Apr. 19, 2022

(54) SYSTEMS AND METHODS FOR LOCATING SOURCES OF FUGITIVE GAS EMISSIONS

(71) Applicant: ABB Schweiz AG, Baden (CH)

(72) Inventors: J. Brian Leen, Sunnyvale, CA (US); Yi-wen Huang, Saratoga, CA (US)

(73) Assignee: ABB Schweiz AG, Baden (CH)

( * ) Notice: Subject to any disclaimer, the term of this patent is extended or adjusted under 35 U.S.C. 154(b) by 184 days.

(21) Appl. No.: 16/692,247

(22) Filed: Nov. 22, 2019

(65) Prior Publication Data
US 2021/0156793 A1    May 27, 2021

(51) Int. Cl.
| | |
|---|---|
| *G01N 21/31* | (2006.01) |
| *G01M 3/04* | (2006.01) |
| *G01C 19/00* | (2013.01) |
| *G01N 33/00* | (2006.01) |
| *G01P 15/18* | (2013.01) |
| *G01S 19/01* | (2010.01) |

(52) U.S. Cl.
CPC ............. *G01N 21/31* (2013.01); *G01C 19/00* (2013.01); *G01M 3/04* (2013.01); *G01N 33/0047* (2013.01); *G01P 15/18* (2013.01); *G01S 19/01* (2013.01); *G01N 2201/12* (2013.01)

(58) Field of Classification Search
CPC ............... G01N 21/31; G01N 33/0047; G01N 2201/12; G01N 21/25; G01N 21/3504; G01M 3/04; G01M 3/16; G01M 3/20; G01C 19/00; G01P 15/18; G01S 19/01; G01S 19/49; F17D 5/005
See application file for complete search history.

(56) References Cited

U.S. PATENT DOCUMENTS

| | | |
|---|---|---|
| 5,297,421 A | 3/1994 | Hosonuma et al. |
| 6,518,562 B1 | 2/2003 | Cooper et al. |
| 6,724,481 B2 | 4/2004 | Makino et al. |
| 6,785,619 B1 | 8/2004 | Homann et al. |
| 7,375,814 B2 | 5/2008 | Reichardt et al. |
| 8,032,123 B2 | 10/2011 | Sakhpara |
| 8,294,899 B2 | 10/2012 | Wong |

(Continued)

FOREIGN PATENT DOCUMENTS

| | | |
|---|---|---|
| EP | 0 448 360 A1 | 9/1991 |
| FR | 2831665 A1 | 5/2003 |

(Continued)

OTHER PUBLICATIONS

Gemerek et al., Fugitive Gas Emission Rate Estimation Using Multiple Heterogeneous Mobile Sensors, 2017 IEEE, 3 pp. (Year: 2017).*

(Continued)

*Primary Examiner* — Toan M Le
(74) *Attorney, Agent, or Firm* — Armstrong Teasdale LLP

(57) ABSTRACT

A fugitive gas detection system includes an inertial measurement assembly that measures a change in position of the inlet of a gas analyzer and applies a time slip to concentration data detected by an analyzer to generate a time series of the concentration of the gas in three-dimensional space. Applying statistical methods, the relative location of the source of the fugitive gas can be established from the time series. Additionally, in some embodiments, the data may be interpolated to establish a map of a plume of the fugitive gas.

24 Claims, 4 Drawing Sheets

(56) References Cited

U.S. PATENT DOCUMENTS

| | | |
|---|---|---|
| 8,781,755 B2 | 7/2014 | Wong |
| 9,435,782 B2 | 9/2016 | Lenz et al. |
| 9,482,591 B2 | 11/2016 | Rella et al. |
| 9,494,511 B2 | 11/2016 | Wilkins |
| 9,500,556 B2 | 11/2016 | Rella et al. |
| 9,557,240 B1 | 1/2017 | Tan et al. |
| 9,618,417 B2 | 4/2017 | Rella et al. |
| 9,719,879 B1 | 8/2017 | Tan et al. |
| 9,978,251 B2 | 5/2018 | Gonia et al. |
| 10,161,825 B2 | 12/2018 | Rella et al. |
| 2004/0050188 A1 | 3/2004 | Richards et al. |
| 2008/0045156 A1 | 2/2008 | Sakhpara |
| 2010/0091267 A1 | 4/2010 | Wong |
| 2012/0028820 A1 | 2/2012 | Rhodes et al. |
| 2013/0110400 A1 | 5/2013 | Moshe |
| 2013/0220036 A1 | 8/2013 | Faust |
| 2014/0318276 A1 | 10/2014 | Cappa et al. |
| 2015/0007638 A1 | 1/2015 | Rella et al. |
| 2016/0146696 A1 | 5/2016 | Steele et al. |
| 2016/0307468 A1* | 10/2016 | Trumbull ............... G09B 5/02 |
| 2018/0172544 A1 | 6/2018 | MacMullin et al. |

FOREIGN PATENT DOCUMENTS

| | | |
|---|---|---|
| GB | 2338072 A | 12/1999 |
| RU | 2519405 C1 | 6/2014 |
| SU | 292097 A1 | 1/1971 |
| SU | 1366908 A1 | 1/1988 |
| WO | 2010/070147 A1 | 6/2010 |
| WO | 2015/052421 A1 | 4/2012 |

OTHER PUBLICATIONS

Zhang et al., Field Deployment of a Portable Optical Spectrometer for Methane Fugitive Emissions Monitoring on Oil and Gas Well Pads, Published: Jun. 16, 2019, Sensors 2019, 19, 2707, 18 pp. (Year: 2019).*

Google Search History, Jun. 30, 2021, 1 pp. (Year: 2021).*

European Search Report for related EP 20208705, completed Apr. 8, 2020, 5 pages.

Jakuba, "Stochastic Mapping for Chemical Plume Source localization with Application to Autonomous Hydrothermal Vent Discovery", downloaded from https://dspace.mit.edu/bitstream/handle/1721.1/38931/166142007-MIT.pdf?sequence=2, Apr. 19, 2007, 325 pages.

"Bio-Inspired and Probabilistic Algorithms for Distrubed Odor Source Localization using Mobile Robots", downloaded from https://infoscience.epfl.ch/record/143049/files/EPFL_TH4628.pdf, 2010, 6 pages.

Ishida et al., "Remote sensing of gas/odor source location and concentration distribution using mobile system", Sensors and Actuators B 49 (1998) 52-57.

Reggente et al., "Using Local Wind Information for Gas Distribution Mapping in Outdoor Environments with a Mobile Robot", IEEE Sensors 2009 Conference, pp. 1715-1720.

Fukazawa et al., "Estimating Gas-Source Location in Outdoor Environment Using Mobile Robot Equipped with Gas Sensors and Anemometer", IEEE Sensors 2009 Conference, pp. 1721-1724.

Neumann et al., "Autonomous Gas-Sensitive Microdrone", IEEE Robotics & Automation Magazine, Mar. 2012, pp. 50-61.

Lilienthal, "Chapter 10, Improved Gas Source Localization with a Mobile Robot by Learning Analytical Gas Dispersal Models from Statistical Gas Distribution Maps Using Evolutionary Algorithms", IGI Global, pp. 249-276, 2011.

McManus et al., "Field measurement of atmospheric methane with a HeNe laser-based real-time instrument", downloaded from https://www.spiedigitallibrary.org/conference-proceeings-of-spie on Mar. 20, 2019, 14 pages.

Hirst et al., "Oil and gas prospecting by ultra-sensitive optical gas detection with inverse gas dispersion modelling", Geophysical Research Letters, vol. 31, L12115, 2004, 4 pages.

"GIS for Petroleum", downloaded from www.ESRI.com/petroleum, Feb. 2007, 32 pages.

Thomson et al., "An improved algorithm for locating a gas source using inverse methods", Atmospheric Environment 41 (2007) 1128-1134.

Lamb et al., "Development of Atmospheric Tracer Methods to Measure Methane Emissions from Natural Gas Facilities and Urban Areas", Envir. Sci. Technol. 1995, 29, 1468-1479.

Leifer et al., In situ sensing of methane emissions from natural marine hydrocarbon seeps A potential remote sensing technology, Earth and Planetary Science Letter 245 (2006) 509-522.

Horst et al., "Footprint Estimation for Scalar Flux Measurements in the Atmospheric Surface Layer", Boundary-Layer Meteorology 59:279-296, 1992.

Lochmatter et al., "Tracking Odor Plumes in a Laminar Wind Field with Bio-Inspired Algorithms", Springer Tracts in Advanced Robotics, Nov. 2008, 16 pages.

Bennetts et al., "Mobile robots for localizing gas emission sources on landfill sites: is bio-inspiration the way to go?", fronteirs in Neuroengineering, Jan. 2012, vol. 4, Article 20, 12 pages.

Meng et al., "Collective Odor Source Estimation and Search in Time-Variant Airflow Environments Using Mobile Robots", Sensors 2001, 11, 29 pages.

Pavlin et al., "Gas Detection and Source Localization: A Bayesian Approach", 2011 IEEE, 8 pages.

Baetz et al., "Mobile Robots with Active IR-Optical Sensing for Remote Gas Detection and Source Localization", 2009 IEEE International Conference on Robotics and Automation, pp. 2773-2778.

Ishida et al., "Remote Sensing and Localization of Gas/Odor Source and Distribution Using Mobile Sensing System", TRASDUCERS '97, 1997 International Conference on Solid-State Sensors and Actuators, pp. 559-563.

Ishida et al., "Three-Dimensional Gas-Plume Tracking Using Gas Sensors and Ultrasonic Anemometer", 2004 IEEE, pp. 1175-1178.

Ishida et al., "Mobile Robot Path Planning Using Vision and Olfaction to Search for a Gas Source", 2005 IEEE, pp. 1112-1115.

Jiang et al., "A Novel Object Recognition Method for Mobile Robot Localizing a Single Odor/Gas Source in Complex Environments", 2008 IEEE, 5 pages.

Wainner et al., "High Altitude Aerial Natural Gas Leak Detection System", Apr. 2007, 100 pages.

* cited by examiner

US 11,307,137 B2

SYSTEMS AND METHODS FOR LOCATING SOURCES OF FUGITIVE GAS EMISSIONS

TECHNICAL FIELD

The present disclosure relates to a method and apparatus for mapping concentrations of fugitive gas emissions to detect and locate the source of the fugitive gas emissions. More particularly, the present disclosure relates to a method and apparatus that utilizes a hand-held detector capable of providing dead-reckoning to map the concentration of fugitive gas emissions and locate the source of the particular fugitive gas emissions.

BACKGROUND

The detection of fugitive gas emissions is of significant concern to both utility providers and the public at large as such fugitive emissions cause economic losses, and, in some cases, may present a danger if the gases are noxious or flammable. A variety of low sensitivity tools currently exist to help utilities identify leaks in their distribution system. These tools generally fall into two categories: hand held and vehicle mounted.

Hand held devices such as flame ionization detectors or infrared (IR) absorption are used by walking surveyors any time a leak is suspected and on a periodic basis to check mains and house service lines for unknown leaks. During a walking survey, the surveyor walks along the main with a handheld wand at above ground service pipes and features likely to emit from underground leaks (e.g., sewer grates, cracks in the roadway, edges of sidewalks, service standpipes, etc.). Large leaks may be detected, but the process is time consuming and, because the handheld devices are only sensitive to concentration changes in the parts per million (ppm) and are slow to respond to changes in gas concentration, this requires the surveyor to check particular locations by holding the wand in a fixed position. As such, this survey technique is time consuming and reserved for detecting leaks at suspect locations.

In other uses, a sensor is placed on a mobile platform as one approach for increasing the speed and sensitivity of detection. For example, an optical methane detector (OMD) offered by Heath Consultants is an IR light source and detector tuned to the absorption band of methane and an open path of about 1.5 meters. The system is sensitivity to about 1 ppm-m of absorption. While operable at driving speeds up to about 15 miles per hour, it has limited sensitivity and must pass within close proximity to a leak source, such as within 25 feet. The sensitivity of mobile sensors is being improved with the use of integrated cavity output spectroscopy (ICOS), which is a methane detector with measurement precision on methane of approximately 2 parts per billion (ppb) and, when paired with a GPS and optional wind measurements, it is possible to detect very small or very remote natural gas leaks.

However, the workflow after a leak is identified using higher sensitivity mobile approaches still requires the surveyor to get out of the vehicle and search the indicated area for leaks using lower sensitivity handhelds. Because handhelds need to be immediately proximate to the leak source to sense gas, surveyors typically spend 30-60 minutes walking with handheld sensors before finding the actual leak location. The long search time is not only costly and frustrating, but in many cases walking surveyors will not find the leak at all. Without a sensor that can detect the gas plume at ppb levels, a walking surveyor's only recourse is to visually identify likely leak locations.

SUMMARY

The present disclosure includes one or more of the features recited in the appended claims and/or the following features which, alone or in any combination, may comprise patentable subject matter.

According to a first aspect of the present disclosure, a gas leak detector comprises an inertial measurement assembly, a high precision gas analyzer, a wand, and a controller. The wand has an inlet tip that receives ambient air and directs the ambient air to the high precision gas analyzer. The wand is physically coupled to the inertial measurement assembly such that movement of the wand is detected by the inertial measurement assembly.

The controller receives signals from the inertial measurement assembly and the high precision gas analyzer. The controller includes a processor and a memory device, the memory device including instructions that, when acted upon by the processor, cause the controller to monitor the signals from the inertial measurement to identify the real-time changes in location of the tip of the wand. The instructions further cause the controller to log the changes in location as a time series. The instructions still further cause the controller to monitor signals from high precision gas analyzer indicative of the concentration of a one or more particular type of fugitive gas dispersed in the ambient air and log the concentration of the particular molecules of each of the one or more particular type of fugitive gas dispersed in the ambient air as a time series. The instructions also cause the controller to apply an adjustment factor dependent on characteristics of the wand to the time series of the concentration of the particular type of fugitive gas in the air to offset the time series such that the measured concentration of the particular type of fugitive gas is aligned with the position of the tip of the wand when the measured concentration entered the wand to create an adjusted concentration time series. The instructions still also cause the controller to log the adjusted concentration time series with the changes in location time series to create a combined time series that includes both position and fugitive gas concentration data.

In some embodiments, the inertial measurement assembly measures three-dimensional changes in position of the inertial measurement assembly and measure changes in the pitch, roll, and yaw of the inertial measurement assembly to provide the signal to the controller indicative of changes in the location of the tip of the wand.

In some embodiments, the inertial measurement assembly includes a structure capable of measuring acceleration in three orthogonal axes.

In some embodiments, the inertial measurement assembly includes a structure capable of measuring gyroscopic deviations about the three orthogonal axes.

In some embodiments, the high precision gas analyzer utilizes integrated cavity output spectroscopy to measure the concentration of a particular type of gas in the ambient air.

In some embodiments, the memory device includes further instructions that, when acted upon by the processor, cause the processor to utilize a Gaussian plume model to evaluate the combined time series that includes both position and concentration data to determine a vector indicative of the likely location of the source of the fugitive gas.

In some embodiments, the memory device includes further instruction that, when acted upon by the processor, cause the processor to utilize a Bayesian estimation to evaluate the combined time series that includes both position and concentration data to determine a vector indicative of the likely location of the source of the fugitive gas.

In some embodiments, the memory device includes further instruction that, when acted upon by the processor, cause the processor to utilize a plurality of winds around the peak of spatial or temporal methane peaks in the combined time series that includes both position and concentration data to determine a vector indicative of the likely location of the source of the fugitive gas.

In some embodiments, the gas leak detector further comprises a user interface in communication with the controller, the memory device including instructions that, when executed by the processor, provide an output to the user interface that causes the user interface to provide a real-time indication of the likely direction and/or location of the source of the fugitive gas relative to the gas leak detector.

In some embodiments, the controller receives a signal from a geospatial position satellite system indicative of a geospatial reference datum while the positional data series is being collected, and wherein the memory device includes instructions that, when executed by the processor, cause the processor to process the real-time changes in position of the inertial measurement assembly to create an adjusted time series of the position data to reference the geospatial location of the tip of the wand, and create a combined time series that includes both geospatial position and fugitive gas concentration data.

In some embodiments, the gas leak detector further comprises a user interface in communication with the controller, the memory device including instructions that, when executed by the processor, provide an output to the user interface that causes the user interface to provide a real-time indication of the likely location of the source of the fugitive gas relative to the gas leak detector.

According to a second aspect of the present disclosure, a method of identifying a source location of a gas leak comprises moving an inlet of a handheld gas analyzer in space to collect ambient air samples, measuring real-time changes in the position of the inlet of the gas analyzer using an inertial measurement assembly, and logging a time series of the changes in position of the inlet. The method further includes measuring the real-time concentration of a particular fugitive gas using a high precision gas analyzer, and adjusting the real-time concentration of the particular fugitive gas with a time slip factor to account for delays in the transfer of the fugitive gas from the inlet to the high precision gas analyzer to generate a time-slipped data series of the concentration. The method also includes combining the time-slipped concentration data series with the time series of changes in position of the inlet to create a time series indicative of the relative position of the inlet and the concentration of fugitive gas at the inlet over time.

In some embodiments, the method further includes determining a reference geospatial position of the inertial measurement assembly during the collection of real-time changes in position, offsetting the time series of the relative position of the inlet with the reference geospatial position to create a time series of the geospatial position of the inlet, and combining the time-slipped concentration data series with the time series of the geospatial position of the inlet to create a time series indicative of the geospatial position of the inlet and the concentration of fugitive gas at the inlet over time.

In some embodiments, the method further includes utilizing a Gaussian plume model to evaluate the combined time series that includes both position and concentration data to determine a vector indicative of the likely location of the source of the fugitive gas, and outputting a visual representation of the likely location of the source of fugitive gas on a display device.

In some embodiments, the method further includes utilizing a Bayesian estimation to evaluate the combined time series that includes both position and concentration data to determine a vector indicative of the likely location of the source of the fugitive gas, and outputting a visual representation of the likely location of the source of fugitive gas on a display device.

In some embodiments, the method further includes processing the time series indicative of the geospatial position of the inlet and the concentration of fugitive gas at the inlet over time with a statistical interpolation to create a three-dimensional data set that approximates the concentration of the fugitive gas in space, and plotting the three-dimensional data set that approximates the concentration of the fugitive gas in space to create a visual representation of the concentration on a map.

According to a third aspect of the present disclosure, a system for measuring the distribution of a fugitive gas in three dimensions comprises an inertial measurement assembly, a high precision gas analyzer, a wand, a user interface, and a controller. The inertial measurement assembly provides a signal indicative of changes in the three-dimensional position and three-axis orientation of the inertial measurement assembly in real-time. The high precision gas analyzer measures the concentration of a gas in real-time. The wand has an inlet tip that receives ambient air and directs the ambient air to the high precision gas analyzer. The wand is physically coupled to the inertial measurement assembly such that movement of the wand is detected by the inertial measurement assembly. The user interface has user input devices and a display. The controller is in communication with the inertial measurement assembly, the high precision gas analyzer, and the user interface, the controller including a processor and a memory device coupled to the processor. The memory device stores instructions that, when executed by the processor cause the user interface to display a prompt a user to input data regarding the configuration of the wand. The instructions cause the processor to receive a signal from the user input devices indicative of the configuration of the wand. The instructions cause the processor to, based on the configuration of the wand, establish a time slip parameter for monitoring ambient air for the concentration of the gas and establish the offset from inlet tip to the inertial measurement assembly. The instructions cause the processor to log a time series that includes the change in position of the tip of the inlet and the time slipped concentration data as the tip of the inlet is moved in space.

In some embodiments, the memory device includes instructions that, when executed by the processor, apply a statistical interpolation to the time series log to create a three-dimensional data set that approximates the concentration of the fugitive gas in space.

In some embodiments, the memory device includes instructions that, when executed by the processor, apply a Gaussian plume model to evaluate the time series that includes the change in position of the tip of the inlet and the time slipped concentration data as the tip of the inlet is moved in space to determine a vector indicative of the likely location of the source of the fugitive gas.

In some embodiments, the memory device includes instructions that, when executed by the processor, apply a Bayesian estimation to evaluate the time series that includes the change in position of the tip of the inlet and the time slipped concentration data as the tip of the inlet is moved in space to determine a vector indicative of the likely location of the source of the fugitive gas.

In some embodiments, the memory devices includes instructions that, when executed by the processor, cause the processor to signal the user interface to prompt a user to input a geospatial reference location and adjust the time series that includes the change in position of the tip of the inlet and the time slipped concentration data as the tip of the inlet is moved in space to convert the changes in location to geospatial location data.

In some embodiments, the memory device includes instructions that, when executed by the processor, apply a Gaussian plume model to evaluate the time series that includes the change in position of the tip of the inlet and the time slipped concentration data as the tip of the inlet is moved in space to determine a geospatial location of the source of the fugitive gas.

In some embodiments, the system further comprises a sonic or mechanical anemometer in communication with the controller, the memory device including instructions that, when executed by the processor, cause the processor to update the time series that includes the change in position of the tip of the inlet and the time slipped concentration data as the tip of the inlet is moved in space to include wind vector information, and, wherein the Gaussian plume model is applied using the wind vector to determine the geospatial location of the source of the fugitive gas.

In some embodiments, the system further comprises an anemometer in communication with the controller, the memory device including instructions that, when executed by the processor, cause the processor to update the time series that includes the change in position of the tip of the inlet and the time slipped concentration data as the tip of the inlet is moved in space to include wind vector information, apply a statistical interpolation to the time series log to create a three-dimensional data set that approximates the concentration of the fugitive gas in space, and generate a visual representation of the distribution of the concentration of the fugitive gas in space on the display of the user interface.

These and other features of the present disclosure will become more apparent from the following description of the illustrative embodiments.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION

Figure 1:
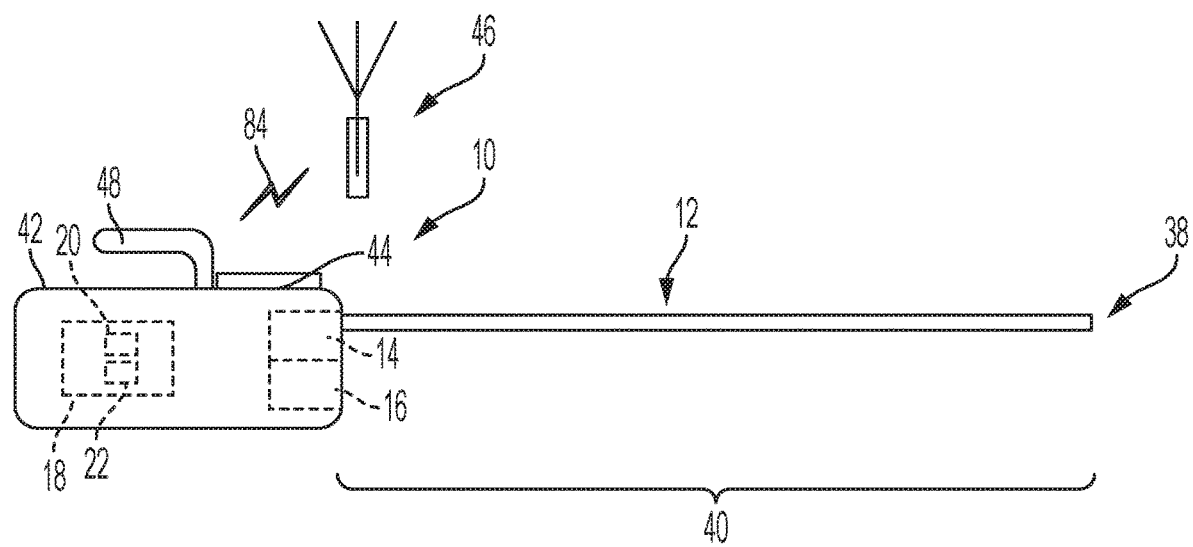
FIG. 1 is a side view of a hand-held gas detector having an on-board gas analyzer and an inertial measurement assembly that detects relative movement of the hand-held gas detector in six axes.

While the concepts of the present disclosure are susceptible to various modifications and alternative forms, specific embodiments thereof have been shown by way of example in the figures and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

A diagrammatic representation of a gas detector 10 according to the present disclosure is shown in FIG. 1 to include a wand 12 which acts as an inlet to a gas analyzer 14. The gas detector 10 also includes an inertial measurement unit (IMU) 16, a user interface 44, and a controller 18. The controller 18 includes a processor 20 and a memory device 22 that includes instructions executed by the processor 20 to operate the gas detector 10 in the manner described below. In some embodiments, the IMU 16 and user interface 44 are controlled by a first processor device of the controller 18 and the gas analyzer 16 is controlled by a second processor device of the controller 18. It should be understood that other configurations of processor devices for operating the functional components of the gas detector 10 may be employed, depending on the processing requirements for each of the functional units.

Figure 3:
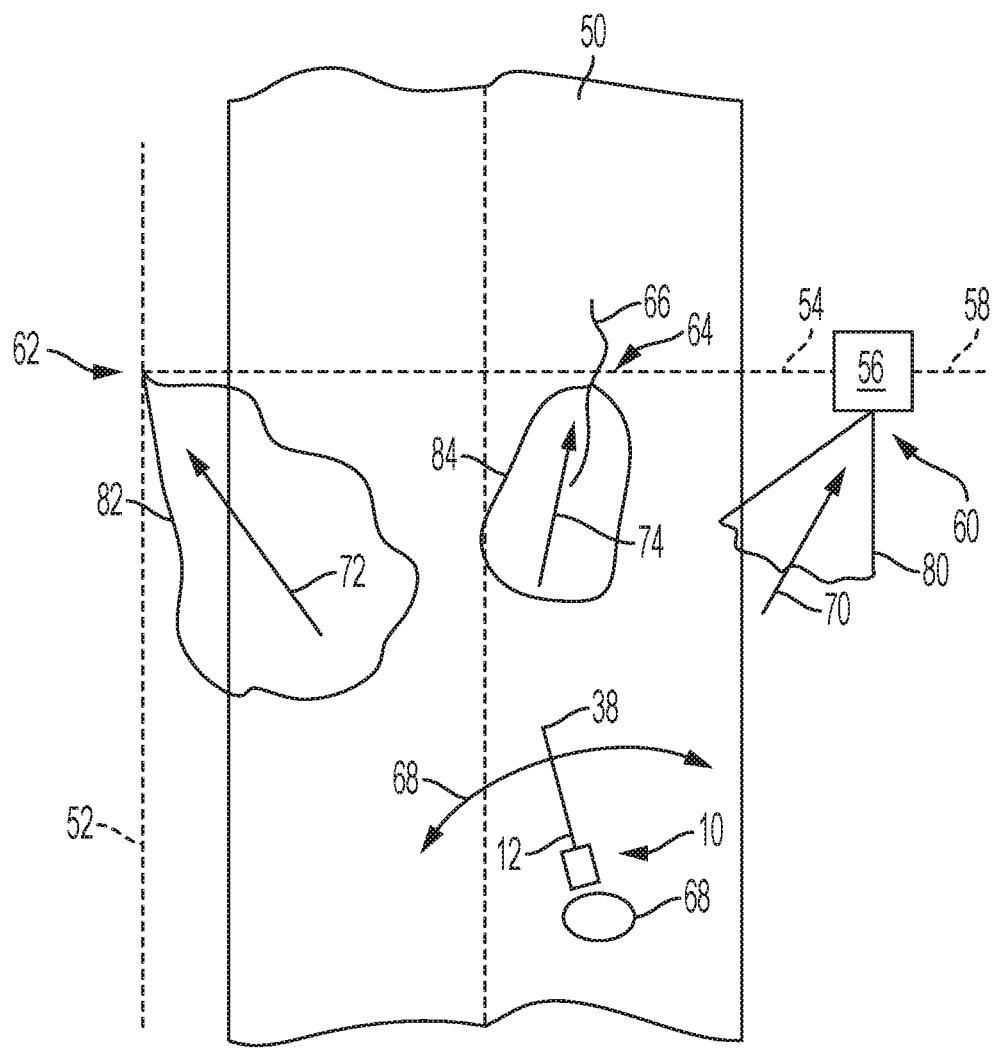
FIG. 3 is a diagrammatic representation of three different gas plumes that emanate from three different leak sources.

An example use of the gas detector 10 is illustrated diagrammatically in FIG. 3 where a portion of a roadway 50 is shown with a gas main 52 positioned underground alongside the roadway 50. An underground service line 54 traverses the roadway and connects to a meter 56 for a particular customer. The meter 56 is connected to a supply line 58 that delivers the metered flow to the customer site.

Three potential leak sources are illustratively depicted in FIG. 3 with a first leak source 60 being a faulty connection at the meter 56, second leak source 62 being a faulty connection between the gas main 52 and service line 54, and a third leak source 64 being a fault in the service line 54 which escapes to the surface through a crack 66 in the surface of the roadway 50. A user 68 moves along the roadway 50 moving the gas detector 10 in space to move a tip 38 of the wand 12 back and forth as indicated by arrow 68. The arrows 70, 72, and 74 represent vectors that may be determined mathematically to provide information to the user to identify the location of each of the sources 60, 62, and 64, respectively, as will be discussed in further detail below. It should be understood that the fugitive gas escaping from each of the leak sources 60, 62 and 64 disperses into plumes 80, 82, and 84 with the concentration of the respective plume varying as the gas dissipates way from the respective sources 60, 62, and 64.

Each of the plumes 80, 82, and 84 has a varying concentration throughout the respective plume 80, 82, and 84 that is a result of the rate of the respective leak source 60, 62, and 64, as well as environmental conditions. The environmental conditions that affect dispersion of the fugitive gas may include ambient temperature, humidity, and wind vectors. The dynamic nature of the variations in concentration throughout the plumes 80, 82, and 84, make modeling the plumes 80, 82, and 84 a complex problem.

Figure 5:
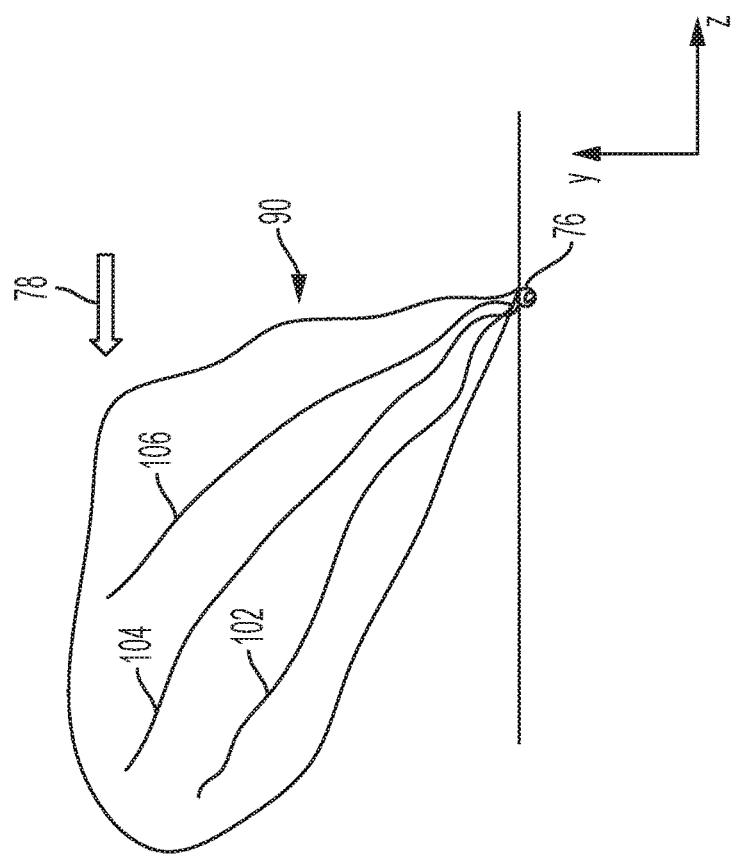
FIG. 5 is a diagrammatic representation of the gas plume emanating from a leak source as viewed along a second direction, the second direction orthogonal to the first direction.
Figure 4:
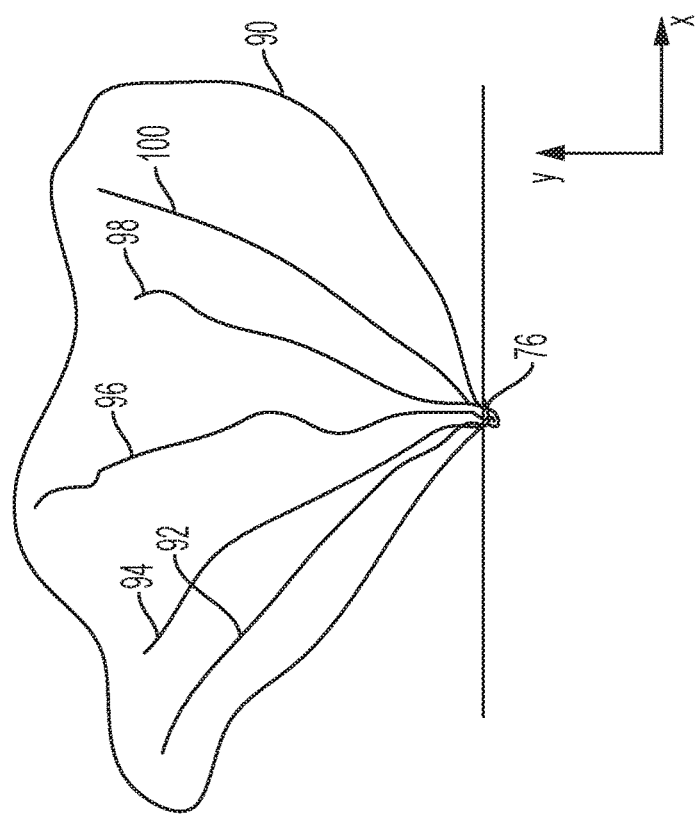
FIG. 4 is a diagrammatic representation of a gas plume emanating from a leak source as viewed along in a first direction.

An example plume 90 is shown in FIGS. 4 and 5. In FIG. 4 a view of the plume 90 emanating from a source 78 is shown in two dimensions, x and y. The same plume 90 is shown in FIG. 5, in the z and y dimensions. A wind vector 78 is shown in FIG. 5 to be acting on the plume 90 in the z direction. The lines 92, 94, 96, 98, 100, 102, 104, and 106 in FIGS. 4 and 5 are diagrammatic representations of the dispersion directions of the concentration of the fugitive gas. It should be understood that as the variation in dispersion, while challenging to model, provides a good indication of the likely location of the source 76 when the concentration data is mapped in three-dimensional space. The gas detector 10 is configured to simplify the data collection for that mapping. Additional statistical techniques, as described below, may be used to draw inferences from the collected data to characterize the shape and location of the plume 90, as well as identifying the likely location of the leak source 76.

Figure 2:
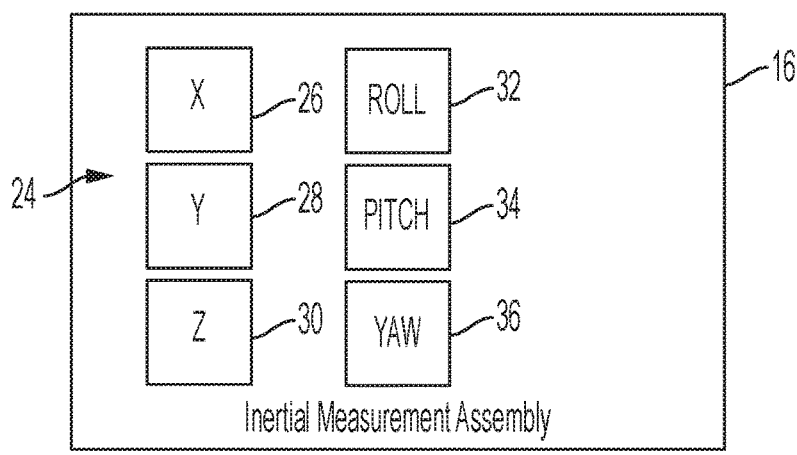
FIG. 2 is a block diagram of the inertial measurement assembly of FIG. 1.

Referring now to FIG. 2, the IMU 16 is shown to include spatial detectors 24 which are embodied as three accelerometers 26, 28, and 30 and three gyroscopes 32, 34, and 36 which cooperate to provide six axes of detection so as to detect the spatial movement of the detector 10, and specifically, a tip 38 of the wand 12, to thereby map the location of the tip 38 in a time series. In some embodiments, the IMU 16 may further include a magnetometer 31 to determine magnetic north, with the three accelerometers 26, 28, and 30 and three gyroscopes 32, 34, and 36, be used to determine the x, y, z, coordinates along with roll, pitch, and yaw. The accelerometers 26, 28, and 30 measure relative movement of the IMU 16 along three-dimensional orthogonal axes. The gyroscopes 32, 34, and 36 measure rotation about the three-dimensional orthogonal axes, i.e. roll, pitch, and yaw. As ambient air enters the tip 38 and is conducted through the wand 12 to the gas analyzer 14, the controller 18 pairs gas concentration data as determined by the analyzer 14 with the relative location of the tip 38 as determined by the IMU 16 to generate a three-dimensional map of the concentration of gas or gases being detected by the gas analyzer 14.

Notably, the IMU 16 is configured to provide dead-reckoning of the location of the detector 10, and, more specifically, the tip 38. The offset location of the tip 38 relative to the IMU 16 is characteristics of the wand 12 which may be known at manufacture, or may be provided by a user if the wand 12 is modified. Using Kalman filtering, or other known methods of extracting relative position data from the IMU 16, the three-dimensional (3D) map of the location of tip 38 is generated without need for real-time absolute global positioning satellite (GPS) position information. This eliminates the reliance of the system on GPS data to accurately map the location, thereby allowing a user to move more quickly than would be possible with a GPS reliant system or operate in an environment that is GPS challenged such as those found between tall buildings or under bridges. The 3D map generated by the IMU 16 may be referenced to a particular location by referencing a datum GPS location while the IMU 16 is collecting data. Thus, a single GPS coordinate may be referenced by the IMU 16 when generating the 3D map. For example, the beginning GPS location may be determined and used as the datum location with the 3D map referenced from the beginning location. Likewise, a datum point may be referenced during the detection process or at the end of the detection process, with the controller 18 operable to offset the detected movements from the GPS datum to generate a 3D map of the location of the tip 38 on an existing site map. The GPS signal may also be used in conjunction with the IMU data. For example, the GPS signal may be included in the Kalman filter along with IMU data to provide a combined estimate of inlet tip location. The extent to which the GPS signal is weighted in the Kalman filter may be increased or decreased according to the GPS signal quality (e.g., satellite count). The reference GPS location may be provided by a GPS sensor resident in the detector 10 and coupled to the controller 18. In the present application, the GPS information is determined from a separate device and input to the user interface 44.

While the IMU 16 provides dead-reckoning of the location of the tip 38, the gas analyzer 14 is constantly analyzing the ambient air entering the tip 38 of the wand 12 to determine the concentration of the gas by using integrated cavity output spectroscopy (ICOS) to detect the concentration of the target gas over time. In other embodiments, detection of the concentration of the target gas may be done with Cavity Ringdown Spectroscopy (CRDS), Harriot cells, White cells, cavity enhanced absorption spectroscopy, mid-infrared laser based absorption spectroscopy, tunable diode laser absorption spectroscopy, or any sensor functioning as a high precision gas analyzer that is sensitive to sub 10 ppb concentrations of methane. In other embodiments, the detector 10 combines the ICOS technology with the dead-reckoning capability of the IMU 16 to combine the position of the tip 38 with the gas concentration data from the gas analyzer 14 to generate a visual representation of the dispersion of the target gas in 3D. Using the combined data from the IMU 16 and the gas analyzer 14, a gas plume may be modeled using statistical interpolation to provide a 3D visualization of the gas plume and assist in determination of the location of the source of the gas plume.

Importantly, the analysis of the dispersion of the gas requires reconciliation of the time delay inherent in the flow of gas through the wand 12 relative to the current location of the tip 38 of the wand 12. This time delay is affected by the length 40 of the wand 12, the internal size of the wand 12, and the flow rate of the gas. By empirical analysis, a time slip factor is determined for a particular configuration and is applied to the detected gas data to provide the appropriate time offset/time slip to account for the position of the tip 38 when the measured value enters the wand 12. Rather than using the real-time concentration data, the combined data series includes the relative position information paired with the time-slipped concentration data to provide an accurate accounting for the offset from the tip 38 of the wand 12 to the gas analyzer 14. The time offset/time slip varies depending on the characteristics of the wand 12 and, in some embodiments, a particular wand 12 may have a zero time offset. Concentration at time (t), is found by selecting the concentration at time (t'), where t'=t+d, where (d) is the delay time.

Figure 6:
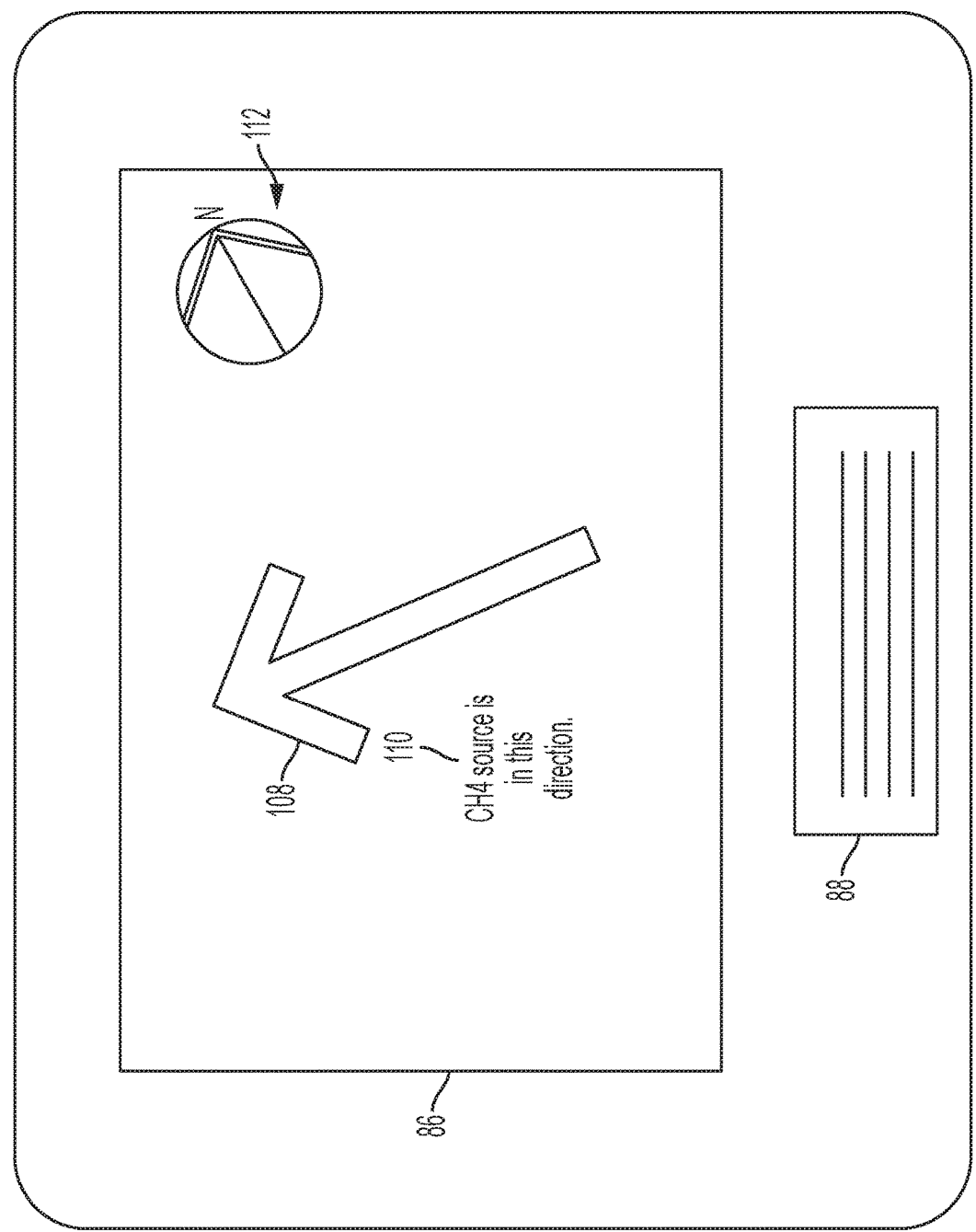
FIG. 6 is a plan view of a user interface of the gas detector of FIG. 1.

In the illustrative embodiment, the wand 12 is connected to a housing 42 of the gas detector 10 as shown in FIG. 1. A user carries the gas detector 10 with a handle 48 and moves the wand 12 in three-dimensions as the user walks across the ground, as suggested in FIG. 3. In the disclosed embodiment, the wand 12 has a length 40 of six (6) feet. In other embodiments, the length 40 could be as short as two (2) feet or as long as thirty (30) feet, depending on the particular use case. It is contemplated that the wand 12 could have a variable length that is adjustable in the field for a particular survey. As noted above, the length 40 is one variable used in the determining the time-slip for the gas concentration data. When different lengths 40 of the wand 12 may be used with a detector 10, the information regarding the characteristics of the wand 12 are input into the controller 18 through the user interface 44. As shown in FIG. 6, the user interface includes a display 86 and a user input device 88, which is a QWERTY keyboard in the illustrative embodiment. In other embodiments, the display 86 may be a touchscreen display with user inputs made on the touchscreen display. The controller 18 communicates independently with each of the user interface 44, analyzer 14, and IMU 16 via a serial peripheral interface (SPI). In other embodiments, the communications between the controller 18, user interface 44 analyzer 14, and IMU 16 uses a bus based standard communications protocol, such as RS-232, RS-485, or other similar communications protocols. In some embodiments, one or more of the user interface 44, analyzer 14, and IMU 16 may communicate with the controller 18 through a wireless connection such as Bluetooth™ or websocket protocols.

As shown in FIG. 1, the gas detector 10 may also be connected to an optional anemometer 46, such as a sonic anemometer which provides real-time wind speed and direction information to the controller 18 such that the wind data may be used to modify the data collected by the detector 10. In the embodiment of FIG. 1, the anemometer 44 communicates with the controller 18 through a wireless connection 84. In other embodiments, the anemometer 44 may connected to the gas detector 10 by a wired connection. The anemometer 44 may be carried by the surveyor, attached to a backpack or other wearable mount, or mounted nearby on, for example, a tripod.

In addition to collecting data to provide visualizations of the gas plume, the controller 18 is operable to provide a determination of the location of the source of fugitive gas. Applying Gaussian principles of plume modeling, the observed data is fit to a model to determine the deviation from modeled values of gas concentration from an emission source in a single dimension. This approach performs a non-linear fit of the observed data to the Gaussian plume model for the particular fugitive gas. By minimizing the difference between the observed data and the modeled gas concentration, the location of a leak can be determined in the observed dimension, x, y, or z. The fit error is minimized by adjusting parameters that model the leak rate, the position, and a wind vector. In some embodiments, separate fits may be performed in each of the three-dimensions x, y, or z to establish a vector for the leak in each dimension. Resolving the three single dimensional vectors into a final 3D vector, the leak source may be obtained. Estimation of the source position may also be accomplished using Bayesian estimation. The estimation of source direction may also be created with very simple methods such as a pointer upwind whenever a temporal or spatial methane maxima is detected.

Referring now to FIG. 6, it can be seen that the display 86 of the user interface 44 may display information conveying the location of the source of the leak of fugitive gas as determined by the Gaussian plume model. For example, an arrow 108 provides an indication of the relative direction of the source of the leak as determined by the Gaussian plume model. The size of the arrow 108 may dynamically vary to provide additional information relative to the location of the source of the leak. Additionally, text 110 may be displayed to provide specific information relative to the location of the source of the leak. In some embodiments, the gas analyzer 14 is operable to detect multiple types of gases such as methane, ethane, propane, or added odorants. In this case, the additional gas types may be indicative of a source type. The text 110 may provide an indication to the user of the predicted source type. Still further, the ratio of two different gases, such as ethane/methane, may assist in identifying the source type of the leak.

In the illustrative embodiment, the detector 10 includes a compass and the absolute direction of North 112 may be dynamically displayed to provide a reference for the user 68 as they are moving the wand 12 to search for the source of the leak. In other embodiments, other methods of conveying the relative location of the source of a leak to a user are used: for example, varying an audible signal, or lighting indicator lamps positioned on the housing 42 of the detector 10. Other indications also may provide an indication of the vertical position of a source of a leak to identify leaks that emanate from a roof or other upper portion of a structure. The display 86 may also be used to display a graphical representation of the detected plume in 3D to assist a user with understanding the gathered data. This is especially useful when nearby leak sources may have overlapping plumes.

While the gas detector 10 has been described as a special purpose device, it should be understood that the principles described herein may be applied using existing hardware, such as personal tablet computers, smartphones, or the like. For example, a tablet computer may be used as an independent controller with a user interface. The tablet computer communicates with a wand that includes an integrated gas analyzer 14 and IMU 16, with the data from the gas analyzer 14 and IMU 16 being fed to the tablet for processing and visualization of the plume or indication of the location of the source of the leak.

It should also be understood that the memory 22 may be sufficient to store historical data that may then be downloaded to another computing device through known methods. Still further, the detector 10 may have cellular or wireless capability allowing data to be transferred from the detector 10 memory 22 to other storage locations, including cloud storage. Storage of the historical data provides the ability to compare plume shapes detected at different points in time or to provide a record of plume characteristics for regulatory or risk management purposes.

The display may also present representations of data collected by other systems that the user may interpret to better guide the search for fugitive emissions. Examples include infrastructure data such as the location of buried pipeline, past inspection results by another handheld survey or from vehicle borne surveys.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A gas leak detector comprising:
    an inertial measurement assembly;
    a high precision gas analyzer;
    a wand having an inlet that receives ambient air and directs all or part of the ambient air to the high precision gas analyzer, the wand physically coupled to the inertial measurement assembly such that movement of the wand is detected by the inertial measurement assembly; and
    a controller receiving signals from the inertial measurement assembly and the high precision gas analyzer, the controller including processor and a memory device, the memory device including instructions that, when acted upon by the processor, cause the controller to:
        monitor the signals from the inertial measurement assembly to identify real-time changes in location of the inlet of the wand;
        log the changes in location;
        monitor signals from the high precision gas analyzer indicative of a concentration of a one or more particular type of fugitive gas dispersed in the ambient air;
        log the concentration of particular molecules of each of the one or more particular type of fugitive gas dispersed in the ambient air;
        apply an adjustment factor based on characteristics of the wand to a time series of the concentration of the particular type of fugitive gas in the ambient air to offset the time series such that the measured concentration of the particular type of fugitive gas is aligned with the location of the inlet of the wand when the measured concentration entered the wand to create an adjusted concentration time series; and
        log the adjusted concentration time series with the changes in location time series to create a combined time series that includes both position and fugitive gas concentration data.

2. The gas leak detector of claim 1, wherein the inertial measurement assembly measures three-dimensional changes in position of the inertial measurement assembly and measure changes in a pitch, a roll, and a yaw of the inertial measurement assembly to provide the signals to the controller indicative of changes in the location of the inlet of the wand.

3. The gas leak detector of claim 1, wherein the inertial measurement assembly includes a structure capable of measuring acceleration in three orthogonal axes.

4. The gas leak detector of claim 1, wherein the inertial measurement assembly includes a structure capable of measuring gyroscopic deviations about three orthogonal axes.

5. The gas leak detector of claim 1, wherein the high precision gas analyzer utilizes integrated cavity output spectroscopy to measure the concentration of a particular type of gas in the ambient air.

6. The gas leak detector of claim 5, wherein the memory device includes further instructions that, when acted upon by the processor, cause the processor to utilize a Gaussian plume model to evaluate the combined time series that includes both position and concentration data to determine a vector indicative of a likely location of a source of the fugitive gas.

7. The gas leak detector of claim 5 wherein the memory device includes further instructions that, when acted upon by the processor, cause the processor to utilize a Bayesian estimation to evaluate the combined time series that includes both position and concentration data to determine a vector indicative of a likely location of a source of the fugitive gas.

8. The gas leak detector of claim 5 wherein the memory device includes further instructions that, when executed by the processor, cause the processor to utilize a plurality of winds around a peak of spatial or temporal methane peaks in the combined time series that includes both position and concentration data to determine a vector indicative of a likely location of a source of the fugitive gas.

9. The gas leak detector of claim 1, wherein the gas leak detector further comprises a user interface in communication with the controller, the memory device including instructions that, when executed by the processor, provide an output to the user interface that causes the user interface to provide a real-time indication of a likely direction and/or location of a source of the fugitive gas relative to the gas leak detector.

10. The gas leak detector of claim 1, wherein the controller receives a signal from a geospatial position satellite system indicative of a geospatial reference datum while a positional data series is being collected, and wherein the memory device includes instructions that, when executed by the processor, cause the processor to process the real-time changes in position of the inertial measurement assembly to create an adjusted time series of position data to reference a geospatial location of the inlet of the wand, and create a combined time series that includes both geospatial position and fugitive gas concentration data.

11. The gas leak detector of claim 10, wherein the gas leak detector further comprises a user interface in communication with the controller, the memory device including instructions that, when executed by the processor, provide an output to the user interface that causes the user interface to provide a real-time indication of a likely location of a source of the fugitive gas relative to the gas leak detector.

12. A method of identifying a source location of a gas leak, the method comprising:
    moving an inlet of a handheld gas analyzer in space to collect ambient air samples;
    measuring real-time changes in a position of the inlet of the handheld gas analyzer using an inertial measurement assembly;
    logging a time series of the changes in position of the inlet;
    measuring a real-time concentration of a particular fugitive gas using a high precision gas analyzer;

adjusting the real-time concentration of the particular fugitive gas with a time slip factor to account for delays in a transfer of the fugitive gas from the inlet to the high precision gas analyzer to generate a time-slipped data series of the concentration; and combining the time-slipped data series of the concentration with a time series of changes in position of the inlet to create a time series indicative of a relative position of the inlet and the concentration of fugitive gas at the inlet over time.

13. The method of claim 12, further comprising:

determining a reference geospatial position of the inertial measurement assembly during the real-time changes in position;

offsetting the time series of the relative position of the inlet with the reference geospatial position to create a time series of the geospatial position of the inlet; and combining the time-slipped concentration data series with the time series of the geospatial position of the inlet to create a time series indicative of the geospatial position of the inlet and the concentration of fugitive gas at the inlet over time.

14. The method of claim 13, further comprising:

utilizing a Gaussian plume model to evaluate the combined time series that includes both position and concentration data to determine a vector indicative of a likely location of a source of the fugitive gas; and outputting a visual representation of the likely location of the source of the fugitive gas on a display device.

15. The method of claim 13, further comprising:

utilizing a Bayesian estimation to evaluate the combined time series that includes both position and concentration data to determine a vector indicative of a likely location of a source of the fugitive gas; and outputting a visual representation of the likely location of the source of the fugitive gas on a display device.

16. The method of claim 13, further comprising:

processing the time series indicative of the geospatial position of the inlet and the concentration of fugitive gas at the inlet over time with a statistical interpolation to create a three-dimensional data set that approximates the concentration of the fugitive gas in space; and plotting the three-dimensional data set that approximates the concentration of the fugitive gas in space to create a visual representation of the concentration on a map.

17. A system for measuring a distribution of a fugitive gas in three dimensions, the system comprising:

an inertial measurement assembly providing a signal indicative of changes in three-dimensional position and three-axis orientation of the inertial measurement assembly in real-time;

a high precision gas analyzer to measure a concentration of a gas in real-time;

a wand having an inlet with a tip that receives ambient air and directs the ambient air to the high precision gas analyzer, the wand physically coupled to the inertial measurement assembly such that movement of the wand is detected by the inertial measurement assembly;

a user interface having user input devices and a display; and a controller in communication with the inertial measurement assembly, the high precision gas analyzer, and the user interface, the controller including a processor and a memory device coupled to the processor, wherein the memory device stores instructions that, when executed by the processor:

cause the user interface to display a prompt a user to input data regarding a configuration of the wand;

receive a signal from the user input devices indicative of the configuration of the wand;

based on the configuration of the wand, establish a time slip parameter for monitoring ambient air for the concentration of the gas and establish an offset from the tip of the inlet to the inertial measurement assembly; and log a time series that includes a change in position of the tip of the inlet and the time slipped concentration data as the tip of the inlet is moved in space.

18. The system of claim 17, wherein the memory device includes instructions that, when executed by the processor, apply a statistical interpolation to the time series log to create a three-dimensional data set that approximates the concentration of the fugitive gas in space.

19. The system of claim 17, wherein the memory device includes instructions that, when executed by the processor, apply a Gaussian plume model to evaluate the time series that includes the change in position of the tip of the inlet and the time slipped concentration data as the tip of the inlet is moved in space to determine a vector indicative of a likely location of a source of the fugitive gas.

20. The system of claim 17, wherein the memory device includes instructions that, when executed by the processor, apply a Bayesian estimation to evaluate the time series that includes the change in position of the tip of the inlet and the time slipped concentration data as the tip of the inlet is moved in space to determine a vector indicative of a likely location of a source of the fugitive gas.

21. The system of claim 17, wherein the memory device includes instructions that, when executed by the processor, cause the processor to signal the user interface to prompt a user to input a geospatial reference location and adjust the time series that includes the change in position of the tip of the inlet and the time slipped concentration data as the tip of the inlet is moved in space to convert the changes in location to geospatial location data.

22. The system of claim 21, wherein the memory device includes instructions that, when executed by the processor, apply a Gaussian plume model to evaluate the time series that includes the change in position of the tip of the inlet and the time slipped concentration data as the tip of the inlet is moved in space to determine a geospatial location of a source of the fugitive gas.

23. The system of claim 21, wherein the system further comprises a sonic or mechanical anemometer in communication with the controller, the memory device including instructions that, when executed by the processor, cause the processor to update the time series that includes the change in position of the tip of the inlet and the time slipped concentration data as the tip of the inlet is moved in space to include wind vector information, and, wherein a Gaussian plume model is applied using a wind vector to determine a geospatial location of a source of the fugitive gas.

24. The system of claim 17, wherein the system further comprises an anemometer in communication with the controller, the memory device including instructions that, when executed by the processor, cause the processor to update the time series that includes the change in position of the tip of the inlet and the time slipped concentration data as the tip of the inlet is moved in space to include wind vector information, apply a statistical interpolation to the time series log to create a three-dimensional data set that approximates the concentration of the fugitive gas in space, and generate a visual representation of the distribution of the concentration of the fugitive gas in space on the display of the user interface.

\* \* \* \* \*